United States Patent [19]

Merry

[11] 4,387,711
[45] Jun. 14, 1983

[54] MEDICAL DEVICE WITH INFLATABLE CUFF

[75] Inventor: Jack D. Merry, Queensbury, N.Y.

[73] Assignee: Mallinckrodt, Inc., St. Louis, Mo.

[21] Appl. No.: 228,978

[22] Filed: Jan. 27, 1981

[51] Int. Cl.³ ............................................. A61M 25/00
[52] U.S. Cl. .................................. 128/207.15; 604/96
[58] Field of Search ............... 128/207.15, 348, 349 B; 264/255; 428/520, 500, 518

[56] References Cited

U.S. PATENT DOCUMENTS

| | | | |
|---|---|---|---|
| 2,477,614 | 8/1949 | Irons | 428/298 |
| 2,934,514 | 4/1960 | Salyer et al. | 128/348 |
| 3,659,612 | 5/1972 | Shiley et al. | 128/207.15 |
| 3,734,100 | 5/1973 | Walker et al. | 128/207.15 |
| 4,151,149 | 4/1979 | Smith | 428/500 |
| 4,239,799 | 12/1980 | Weinberg | 428/518 |
| 4,320,175 | 3/1982 | Hisazumi et al. | 428/518 |
| 4,331,142 | 5/1982 | Degen | 128/207.15 |

OTHER PUBLICATIONS

Bernhard et al, "Physical Characteristics of and Rates of Nitrous Oxide Diffusion into Tracheal Cuffs", Anesthesiology 48: 413-417; 1978.

*Primary Examiner*—Henry J. Recla
*Attorney, Agent, or Firm*—Bernard, Rothwell & Brown

[57] ABSTRACT

A medical device, such as a tracheal tube, having a cuff for blocking a bodily passage, such as the passage through the trachea, is provided. The cuff is made of a material having a low diffusion rate for nitrous oxide and oxygen relative to the diffusion rate for nitrogen so that, for example, when nitrous oxide is provided as an anesthetic during a surgical procedure in which the tracheal tube is utilized, excessive pressure build-up does not occur within the cuff and post-operative trauma in the tracheal area is avoided. Polyvinylidine chloride-polyvinyl chloride copolymer is disclosed as a suitable material.

1 Claim, 2 Drawing Figures

MEDICAL DEVICE WITH INFLATABLE CUFF

BACKGROUND OF THE INVENTION

1. Field of the Invention

This invention relates to medical devices with inflatable cuffs and more particularly to such devices intended for use in connection with nitrous oxide and oxygen administration.

2. Description of the Prior Art

In connection with surgical procedures, a medical device such as a tracheal tube may be employed. A tracheal tube usually includes an elongated tube adapted to be inserted through the mouth and to extend through the trachea and into communication with the lung area. Such tubes normally include an inflatable cuff positioned in the tracheal area and inflatable to engage the trachea and block the passage of fluid through the tracheal area exteriorly of the elongated tube. A smaller tube contiguous to the larger elongated tube may be provided for conducting air under suitable pressure to the cuff for inflating the cuff. The distal end of this small tube is connected to the interior of the cuff for this purpose. Alternatively, a small lumen may be formed in the wall of the elongated tube and connected to the interior of the cuff to provide a passage for air to inflate the cuff.

It is desirable that excessive pressure within the cuff be avoided because it is believed that when the pressure within the cuff exceeds the venous pressure in the capillary bed of the trachea, post-operative trauma may result.

In connection with some surgical procedures, nitrous oxide ($N_2O$) may be employed as an anesthetic. Present cuffs employed with such tracheal tubes are made of plasticized polyvinyl chloride. It has been found that nitrous oxide diffuses through a wall of such material at a substantially greater rate than the diffusion rate of nitrogen ($N_2$) therethrough. (Nitrogen makes up approximately 80% of content of air.) As a result, the pressure within the cuff may rise to an undesirably high level.

In other cases, a patient may be supplied over a period of several days with an enriched air supply comprising, for example, 40% oxygen, using a tracheal tube of the type described above. When the cuff is made of conventional polyvinyl chloride material, a problem of excessive pressure within the cuff may again be encountered. Oxygen tends to diffuse through such material at a slightly higher rate than nitrogen, and hence the oxygen-enriched air supplied to the patient, which comprises 40% oxygen compared to 20% oxygen in the air supplied for inflating the cuff, tends to diffuse through the cuff from the exterior more rapidly than the air within the cuff diffuses outwardly. As a result, the pressure within the cuff may build over a period of several days to an undesirably high level.

All prior art methods known to the applicant have been directed toward mechanical means for limiting the pressure in the cuff, for example, by incorporating a pressure regulator in the air supply to the cuff to control the pressure in the cuff. These mechanical means have involved undesirable inconvenience, expense and performance compromises.

In accordance with the present invention, the cuff is made of a material which has a significantly lower diffusion rate for nitrous oxide and oxygen in relation to the diffusion rate for nitrogen, so that any pressure build-up is at a lower rate and the pressure does not reach a level which causes trauma to the trachea within the time frame of most anesthesia procedures.

It is an object of this invention to provide a medical device, such as a tracheal tube, having an inflatable cuff which is formed of a material having a lower diffusion rate for nitrous oxide and oxygen than materials presently employed for such cuffs.

SUMMARY OF THE INVENTION

In carrying out this invention, in one form thereof, a medical device, for example a tracheal tube which comprises an elongated tube adapted to extend through the mouth of the patient, through the trachea and into communication with the lung area is provided. An inflatable cuff is positioned on the exterior of the elongated tube and the ends of the cuff are secured in sealed relationship to the exterior wall of the elongated tube. A small passage is provided exteriorly of the elongated tube or within the wall of this tube for supplying air to the interior of the cuff for inflating the cuff. In accordance with this invention, the cuff is formed from a material having a lower diffusion rate for nitrous oxide and oxygen relative to the diffusion rate for nitrogen than the diffusion rate for materials conventionally employed for cuffs so that, when nitrous oxide is provided as an anesthetic during a surgical procedure in which the tracheal tube is utilized or when oxygen-enriched air is supplied to a patient over a prolonged period utilizing the tracheal tube, excessive pressure build-up does not occur within the cuff.

DESCRIPTION OF THE PREFERRED EMBODIMENT

Figure 1:
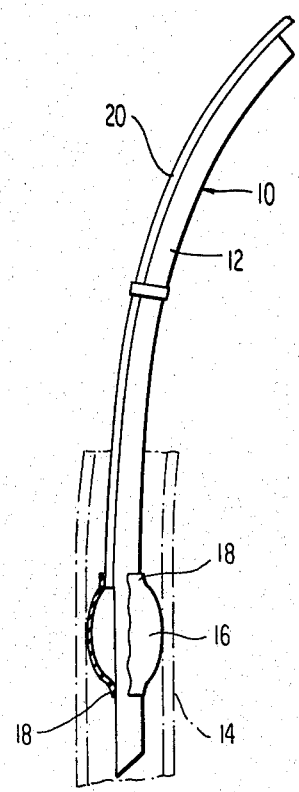
FIG. 1 is a view of a portion of a tracheal tube inserted through the trachea, with the cuff shown in its inflated condition.

Referring to FIG. 1, there is shown a medical device, in the form of a tracheal tube 10 including an elongated tube 12 adapted to be inserted into the tracheal area shown generally at 14. The tube includes an inflatable cuff 16 shown in its inflated condition wherein it engages the wall of the trachea and blocks the passage of fluid therethrough. The ends of the cuff are connected in sealed relationship at 18 to the exterior wall of the elongated tube 12.

In the form of the invention shown in FIG. 1, a second tube 20 of small diameter is shown extending along the exterior wall of the elongated tube 12. The end of the tube 20 extends into the interior of the inflatable cuff 16 so that air may be supplied from any suitable external source through the tube 20 to inflate the cuff to the proper pressure for engaging the trachea and blocking the passage exteriorly of the tube 12. Alternatively, a minor lumen can be formed in the wall of the elongated tube 12 to provide a passage for supply of air to the interior of the cuff 16.

In some surgical procedures in which a tracheal tube of this type is employed, nitrous oxide is utilized as an anesthetic. The nitrous oxide in the lung area contacts the exterior wall of the cuff 16 and, where the cuff is made of a conventional material such as polyvinyl chloride, the nitrous oxide diffuses through the wall at a significantly greater rate than the nitrogen contained in the air supplied to the interior of the cuff. The nitrous oxide also diffuses through the wall of the cuff at a greater rate than the oxygen in the air. Specifically, where the cuff is made of polyvinyl chloride, nitrous oxide has a relatively rapid diffusion rate, while oxygen diffuses more slowly and nitrogen even more slowly. As a result, where the surgical procedure lasts for two or three hours, which is not unusual, the pressure within the cuff may build up to a substantial degree so that the pressure within the cuff exceeds the venous pressure in the capillary bed of the trachea. As indicated earlier in this specification, this excessive pressure is believed to be a significant factor in post-operative tracheal trauma.

On other occasions, it may be necessary to supply a patient with oxygen-enriched air, comprising approximately 40% oxygen, over a prolonged period of several days, again utilizing a tracheal tube of the general type illustrated in FIG. 1. While oxygen diffuses at a relatively slow rate compared to the diffusion rate for nitrous oxide through a cuff made of conventional polyvinyl chloride, it still diffuses at a higher rate than nitrogen. Since the oxygen-enriched air contacting the exterior of the cuff comprises 40% oxygen compared to 20% oxygen and 80% nitrogen in the air within the cuff, the oxygen-enriched air exteriorly of the cuff tends to diffuse more rapidly through the wall of the cuff to the interior of the cuff than the nitrogen in the cuff diffuses outwardly through the wall. Over a period of several days this may cause an undesirably high build-up of pressure within the cuff.

In accordance with the present invention, the cuff 16 is made of a material having a lower diffusion rate for nitrous oxide and oxygen relative to the diffusion rate for nitrogen than the diffusion rate for materials conventionally employed for inflatable cuffs at the present time, for example polyvinyl chloride. More specifically, the cuff 16 is made of a polyvinylidine chloride-polyvinyl chloride copolymer which the applicant has found has the characteristic of a relatively low diffusion rate for nitrous oxide and oxygen. As a result, the pressure build-up over the period occupied by a normal surgical procedure is very much less than would occur utilizing a tracheal tube having a conventional cuff.

Figure 2:
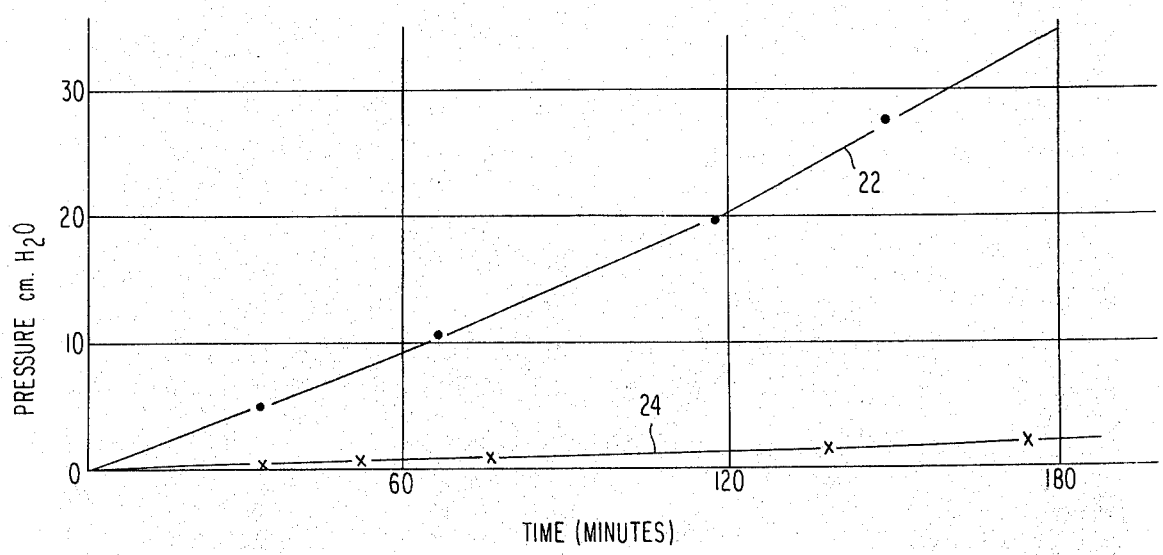
FIG. 2 is a graph comparing the pressure increase over a period of time utilizing a prior art tracheal tube cuff material and utilizing the cuff material of this invention.

This is illustrated in FIG. 2 which represents a comparison of test results utilizing in one case a membrane formed of polyvinyl chloride and in the other case a membrane formed, in accordance with this invention, of polyvinylidine chloride-polyvinyl chloride copolymer, a material which is available from Dow Chemical Company under the trademark "Saran". Referring now to FIG. 2, the upper curve 22 illustrates test results obtained with a membrane made of polyvinyl chloride, and the lower curve 24 illustrates test results obtained with a membrane, in accordance with this invention, made from polyvinylidine chloride-polyvinyl chloride copolymer. It can be seen from FIG. 2 that over a period of three hours, which would not be an abnormally long surgical procedure, where nitrous oxide is used as an anesthetic, the build-up in pressure through a conventional membrane exceeds 30 centimeters of water whereas the build-up of pressure through a membrane formed of the material of the present invention is approximately 2 centimeters.

While the increase in pressure where oxygen-enriched air is being supplied to a patient would not be nearly so rapid using a conventional cuff compared to the pressure rise where nitrous oxide is involved, since the diffusion rate for oxygen is much lower than for nitrous oxide, oxygen-enriched air may be supplied to a patient over several days rather than over two to three hours, and the total increase in pressure may still reach an undesirable level. With the cuff of the present invention this increase in pressure within the cuff is at a much lower rate because of the lower diffusion rate of oxygen, therethrough compared to the diffusion rate through materials presently employed for cuffs. and it is unlikely to reach an excessive level during the period of time during which oxygen-enriched air may be supplied.

Where a cuff made of polyvinylidine chloride-polyvinyl chloride copolymer is employed with an elongated tube made of polyvinyl chloride the ends 18 of the cuff may be readily sealed to the elongated tube by using tetrahydrofuran. This material attacks both polyvinyl chloride and polyvinylidine chloride-polyvinyl chloride copolymer to a sufficient degree to produce a satisfactory weld-type solvent bond. Cyclohexanone, while attacking these materials to a lesser degree, has also been found to produce a satisfactory bond. Alternatively, heat sealing may also be employed as a means of attaching the cuff edges to the elongated tube and to provide a smooth transition at these edges.

While the invention has been described as applied to a tracheal tube and this is an important aspect of the invention, it may also be utilized in other medical devices where similar conditions are present. For example, it may be utilized with a tracheostomy tube or as an esophageal tube. It is intended, therefore, to cover by the appended claims all modifications which come within the spirit and scope thereof.

It is claimed:
1. A medical device comprising:
(a) an elongated tube;
(b) an inflatable cuff surrounding said tube, said cuff being inflatable by air supplied thereto to engage the wall of a body cavity; said cuff being formed of polyvinylidene chloride-polyvinyl chloride copolymer.

* * * * *